United States Patent
Van Der Rijt et al.

(10) Patent No.: US 8,636,677 B2
(45) Date of Patent: Jan. 28, 2014

(54) INTRAORAL APPLIANCE FOR CLEANING TEETH

(75) Inventors: Joost Adrianus Johannes Van Der Rijt, Helmond (NL); Michiel Allan Aurelius Schallig, Drachten (NL); Martinus Bernardus Stapelbroek, Frieschepalen (NL); Jozef Johannes Maria Janssen, Herten (NL); Folkert Vrijburg, Drachten (NL)

(73) Assignee: Koninklijke Philips N.V., Eindhoven (NL)

( * ) Notice: Subject to any disclaimer, the term of this patent is extended or adjusted under 35 U.S.C. 154(b) by 789 days.

(21) Appl. No.: 12/599,738

(22) PCT Filed: May 8, 2008

(86) PCT No.: PCT/IB2008/051834
§ 371 (c)(1),
(2), (4) Date: Aug. 30, 2010

(87) PCT Pub. No.: WO2008/142600
PCT Pub. Date: Nov. 27, 2008

(65) Prior Publication Data
US 2010/0324460 A1   Dec. 23, 2010

Related U.S. Application Data

(60) Provisional application No. 60/939,413, filed on May 22, 2007.

(51) Int. Cl.
*A61H 13/00*  (2006.01)
*A61C 17/22*  (2006.01)

(52) U.S. Cl.
USPC ............ 601/139; 601/46; 601/84; 15/21.1; 15/22.3; 433/216

(58) Field of Classification Search
USPC .............. 601/46, 49, 51, 53, 54, 60, 61, 65, 601/67–70, 82–85, 89, 92, 93, 97, 101, 103, 601/112, 139, 142; 15/21.1, 22.1, 22.2, 25, 15/26, 167.2, 22.3; 433/216, 37–39
See application file for complete search history.

(56) References Cited

U.S. PATENT DOCUMENTS 2,766,750 A   10/1956   Darcissac
5,523,745 A    6/1996   Fortune et al.
(Continued)

FOREIGN PATENT DOCUMENTS

DE         20120955 U1    5/2002
DE    102005009965 A1   12/2006
(Continued)

*Primary Examiner* — Patricia Bianco
*Assistant Examiner* — Kari Petrik

(57) ABSTRACT

The self-contained intraoral appliance includes first and second substantially rigid bands (12, 14) configured to fit along the outer and the inner surfaces of a row of teeth in the mouth. A motor (20) driven by a battery is connected to the bands through a connecting assembly (2, 24, 28, 34, 40 and 44) in such a manner that one end of the first band moves through a displacement to brush the teeth while the other end remains substantially stationary, and such that an opposing end of the second band moves through a displacement while the other end remains substantially stationary. Brush elements (16, 18) are mounted on the surfaces of the bands to provide cleansing of the teeth.

9 Claims, 3 Drawing Sheets

(56) References Cited

U.S. PATENT DOCUMENTS

| | | |
|---|---|---|
| 5,760,692 A | 6/1998 | Block |
| 6,353,956 B1 | 3/2002 | Berge |
| 6,893,259 B1 | 5/2005 | Reizenson |
| 7,071,844 B1 | 7/2006 | Moise |
| 2002/0152563 A1* | 10/2002 | Sato .............................. 15/22.1 |
| 2006/0064037 A1 | 3/2006 | Shalon et al. |

FOREIGN PATENT DOCUMENTS

| | | |
|---|---|---|
| WO | 2005107638 A1 | 11/2005 |
| WO | 2006114291 A2 | 11/2006 |

* cited by examiner

INTRAORAL APPLIANCE FOR CLEANING TEETH

This invention relates generally to appliances for cleaning teeth and/or massaging gums, and more specifically to power brush and massaging appliances which are self-contained within the mouth.

In oral healthcare appliances, there is a continuing need and motivation for an appliance which produces effective cleaning of the teeth. While there are many appliances on the market which, when used properly, produce effective cleaning, it is recognized that the persistence and to some extent the skill of the user plays an important part in cleaning effectiveness. In some cases, the recommended brushing time is not followed because it is perceived to be too long and hence inconvenient. There is also sometimes difficulty in maintaining a consistent desired pressure against the teeth and/or gums.

There are some power appliances which have been designed to minimize the human factor in cleaning teeth. For instance, some power intraoral appliances have been developed which provide an automatic cleaning of the teeth. However, such devices are usually cumbersome to use and involve an external drive assembly which is tethered to the appliance in the mouth. With tethered devices, it is difficult to close the mouth, leading to undesirable exit of saliva and toothpaste, as well as in some cases producing lip irritation. Appearance is also a disadvantage. With such disadvantages, individuals have been reluctant to use them on a long-term basis.

Accordingly, it would be desirable to have an intraoral device which is self-contained and produces effective cleaning, and/or gum massaging, while being convenient as well as safe to use.

Accordingly, one arrangement of the appliance is a self-contained intraoral dental apparatus for cleaning teeth, comprising: a first substantially rigid band configured to fit along the outer surfaces of at least one row of teeth in the mouth; a second substantially rigid band configured to fit along the inner surfaces of said one row of teeth; a motor assembly, including a battery, for driving the first and second bands; an assembly connecting the motor to the first and second bands such that one end of the first band moves through a displacement path while the other end remains substantially stationary, and such that one end of the second band moves through a displacement path while the other end thereof remains substantially stationary; and brush elements attached to the bands, with such a configuration that the teeth are cleaned in operation of the appliance.

Another arrangement is a self-contained intraoral dental appliance for cleaning teeth, comprising: a first substantially rigid band configured to fit along the outer surface of at least one row of teeth in the mouth; a second substantially rigid band configured to fit along the inner surfaces of said at least one row of teeth; at least one motor assembly, including a battery therefor, wherein the motor has a motor body connected by a plate to ends of the first and second bands, one motor assembly having a drive shaft and an eccentric weight attached to the drive shaft, which in operation is free running; and brush elements attached to the bands, with such a configuration that the teeth are cleaned in operation of the appliance.

Another arrangement is a self-contained intraoral apparatus for massaging gums, comprising: a first substantially rigid band configured to fit along the outer surfaces of the upper or lower gums in the mouth; a second substantially rigid band configured to fit along the inner surfaces of said upper or lower gums; a motor assembly, including a battery, for driving the first and second bands; an assembly connecting the motor to the first and second bands such that one end of the first band moves through a displacement path while the other end remains substantially stationary, and such that one end of the second band moves through a displacement path while the other end thereof remains substantially stationary; and massage elements attached to the bands, with such a configuration that the gums are massaged in operation of the appliance.

FIGS. 1-4 show several embodiments of a self-contained power intraoral appliance designed to be positionable for operation entirely within the mouth. No external drive assembly or power source is necessary. The appliance includes a motor which drives opposing portions of the appliance in such a manner that such portions of the appliance move in a generally small circular motion, particularly when bristles with normal length filaments are used on the appliance. Such motion is like that recommended by dentists for a manual toothbrush, producing effective cleansing action of the teeth. Other motions could, however, be produced, including for instance, up/down motion or side-to-side.

Figure 1:
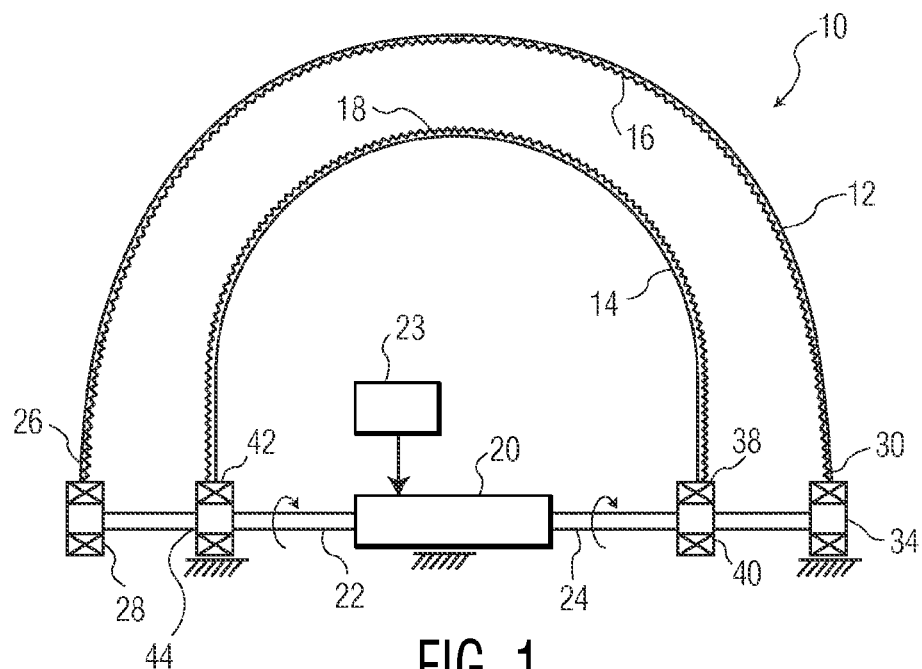
FIG. 1 is a top view of a first embodiment of a power intraoral appliance.

FIG. 1 shows a first embodiment of the appliance 10. It includes a first or outer substantially rigid band 12 which is configured generally to fit along the exterior surfaces of a row of teeth, for example the upper teeth in the mouth. The appliance can also be used for the lower teeth or it can be used for the upper and lower teeth simultaneously, if the band is driven so that the moving bristles cover a large enough area. A second or inner substantially rigid band 14 is configured and arranged relative to the first band 12 such that it fits along the inner surfaces of the teeth. Band 14 will also in operation cover a single row of teeth, either upper or lower, or both upper and lower rows simultaneously. The bands with the attached bristles can also be configured to clean the top surfaces of the teeth, i.e. the molars, in addition to the outer and inner surfaces.

The first and second bands 12, 14 can be made of various materials and combinations of materials, including, for instance, metal, plastic, or ceramic, among others. Mounted on the interior surfaces of the first and second bands are brush elements, shown generally at 16 and 18. The brush elements can be typical brush elements for cleaning teeth, such as nylon bristles used in well-known power toothbrushes.

Further, the inner surface of the first and second bands can be coated or lined with soft material, such as foam or elastomers, which increases the comfort of the device in the mouth. The liner can include various plastics, such as nylon, Teflon, polyesters, or various elastomeric fibers, such as natural or silicone rubber or thermoplastic elastomers, as well as ribbed (roughened) surface structures, such as found in some toothbrushes and tongue scrapers. The top surfaces of the teeth are cleaned with a flat surface with interior rubber, brush or roughened liners.

FIG. 1 includes a motor 20, driven by a battery 23, with drive shafts 22 and 24 extending from opposing ends thereof. The drive shafts 22, 24 extend approximately 90° to the ends of the first and second bands 12 and 14. End 26 of the first band 12 is eccentrically mounted to the end of drive shaft 22 by means of a bearing member 28. As the motor and driveshaft 22 rotate in operation, end 26 of the first band traverses a path with a selected displacement depending upon the size of the connecting bearing 28. This determines the displacement of the brush element at end 26, which will typically be sufficient to cover the back teeth. The other end 30 of the first band 12 is concentrically mounted to drive shaft 24 by a fixedly mounted connecting bearing 34. As the drive shaft 24 moves, end 30 of band 12 will remain fixed.

One end 38 (opposing end) of the second or inner band 14 is eccentrically mounted on the driveshaft 24 by means of a connecting bearing 40. The other end 42 of the second band 14 is concentrically mounted on drive shaft 22 by a connecting bearing 44 which is fixed in position. In operation, the one end 38 of band 14 will move through a selected displacement, depending on the configuration and arrangement of bearing 44, while the other end 42 remains fixed.

The appliance may be operated first for a selected time, and then flipped over and again operated to provide cleaning for both the upper and lower teeth surfaces. The device can also be configured to clean the upper and lower teeth simultaneously. The necessary time to clean is quite short, since all the teeth in the upper and/or lower rows are cleaned at once. Typically, 4-6 seconds will provide the desired cleaning. This is the same amount of time that each tooth is cleaned with a conventional power toothbrush being operated for the recommended time of two minutes.

The brush configuration will also be significant in the cleaning, as the width/length of the bristles may vary along the length of the first and second bands so as to provide complete cleaning coverage of the teeth. The bristles can be configured to accommodate the variation in teeth size between individuals, so as to have a one-size-fits-all effect. Alternatively, a mouthpiece can be used that fits the drive train frame and bands. The mouthpiece could be custom-made or it could be made with impression-type material, with the aid of a dental professional. In the embodiment shown, the motor typically operates in the range of 30-150 Hz, but could in some cases go down to 5 Hz and still produce effective results.

As indicated above, the appliance of FIG. 1 can be used for the upper teeth and then again for the lower teeth or for both simultaneously. The eccentric and concentric mounting of the respective ends of the two bands results in a movement of the bands, and hence the brush elements thereon, toward and away from each other, vertically up/down, or a generally small circular motion, on the surface of the teeth, producing cleansing action on both the inner and outer surfaces of the teeth, as well as on the top surface of the molars.

Figure 2:
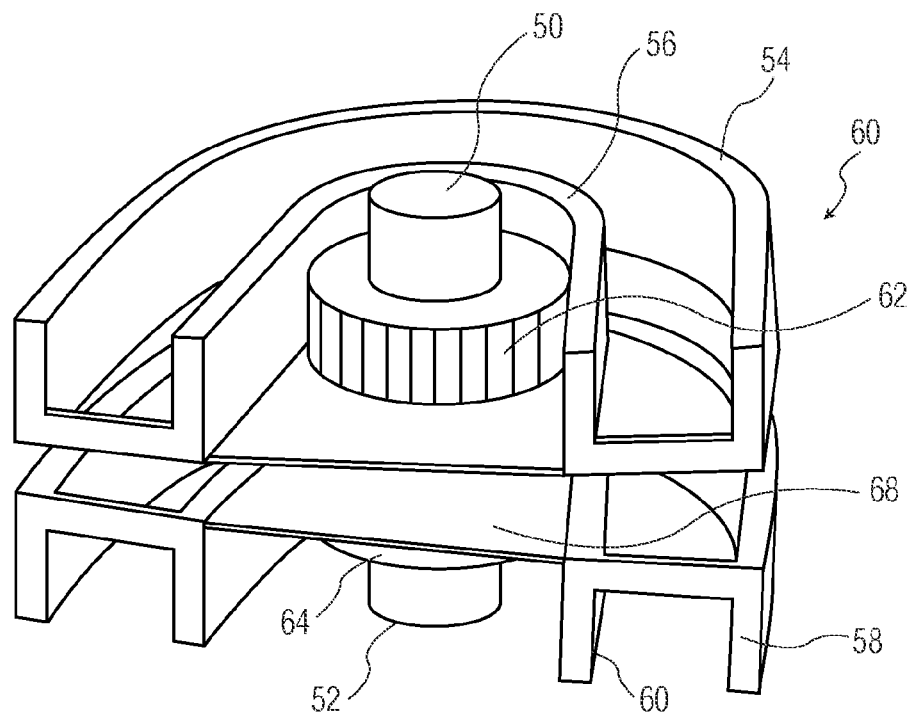
FIG. 2 is a perspective view of a second embodiment of a power intraoral appliance.

FIG. 2 shows a second embodiment, in which the battery powered motor in the appliance 60 is arranged so that its drive shafts 50 and 52 extend vertically in the mouth of the user. The appliance includes first and second substantially rigid bands 54 and 56 and second and third rigid bands 58 and 60, each pair of bands being designed to fit adjacent the exterior and inner surfaces of the upper and/or lower teeth of the user as well as the top surface of the molars. However, it should be understood that the embodiment of FIG. 2 could be designed with just one set of bands. The motor is connected to the respective bands by connecting bearings 62 and 64 and associated plates 66 and 68, referred to as swash plates. The swash plates 66, 68 are driven by the motor. The motor is positioned at an angle relative to the pairs of bands and the swash plates (positioned approximately 15° from the vertical in the embodiment shown), which results in a generally circular movement of the individual bands relative to each other, producing the desired brushing action, in similar fashion to the action of the bands in FIG. 1, as the opposing drive shafts from the motor rotate. The rotation speed range of the motor in this embodiment is similar to that of the first embodiment.

Figure 3:
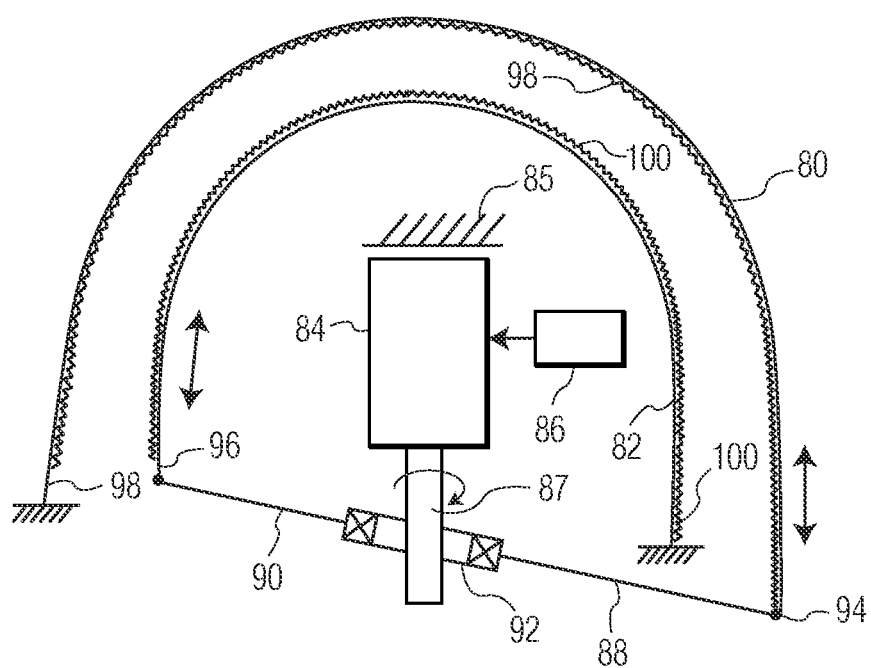
FIG. 3 is a top view of another embodiment of a power intraoral appliance.

FIG. 3 shows a further embodiment, which includes inner and outer bands 80 and 82 and a motor 84 which is fixed in position at one end 85. Motor 84 is powered by a battery 86. Motor 84 is oriented in the plane of bands 80 and 82, extending from front to back of the mouth. Bristles 98 and 100, respectively, are secured to the two bands. A drive shaft 87 extends parallel with the end portions of the bands 80 and 82, as shown. Drive shaft 87 rotates in operation, driving angled swash plates 88 and 90, by means of a connecting bearing 92, the swash plates being attached to one end 94 of the outer band 80 and one end 96 of inner band 82. The other end 98 of outer band 80 and the other end 100 of the inner band 82 are both fixed in position. The swash plates 88 and 90 and the bearing 92 extend at an angle to the drive shaft and ends 94 and 96 of the two bands. The angle is approximately 15°, similar to that of FIG. 2. In operation, a brushing action similar to the previous embodiments occurs.

Figure 4:
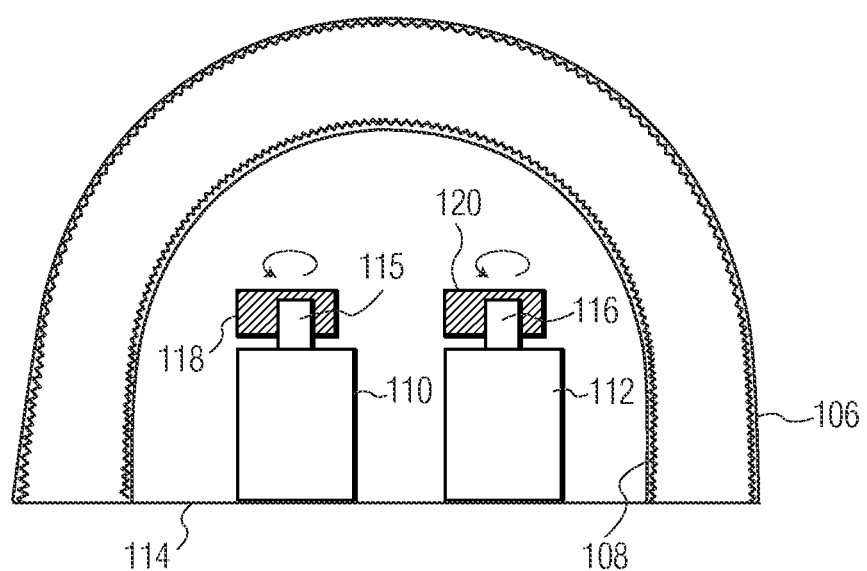
FIG. 4 is a top view of a further embodiment of a power intraoral appliance.

FIG. 4 shows a still further arrangement involving outer and inner bands 106 and 108. Two motors 110 and 112 are shown connected through their respective motor bodies to a plate 114 which is connected to the ends of both the inner and outer bands 106 and 108, shown. Alternatively, just one motor could be used. The drive shafts 115 and 116 of the motors extend from the motors away from plate 114. The drive shafts have eccentrics 118 and 120 mounted on them. In operation, the motors run free. The respective eccentrics vibrate the mouthpiece, producing the desired cleaning action. The speed of motors 110 and 112 is similar to the other embodiments.

Figure 5:
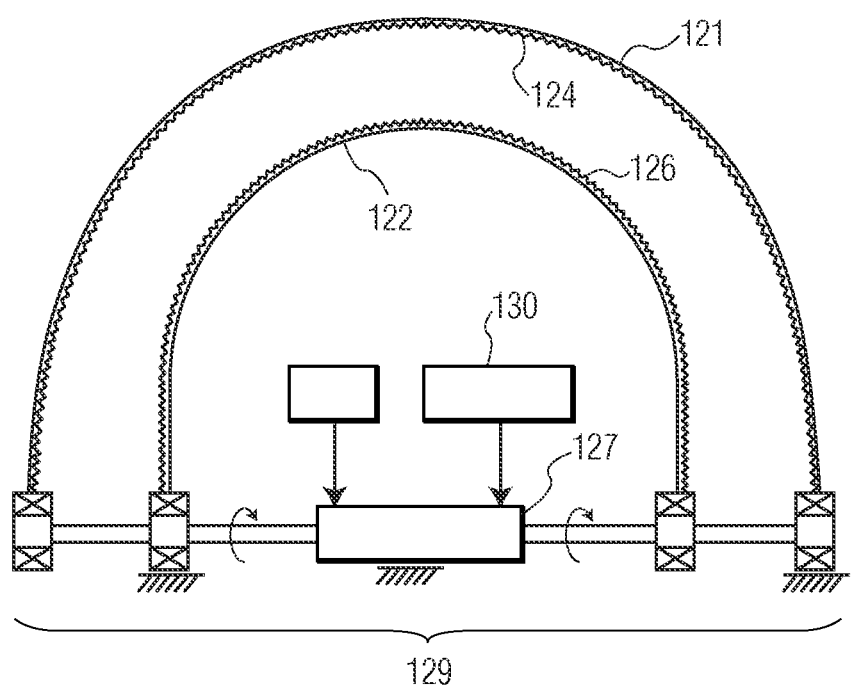
FIG. 5 is a top view of an intraoral appliance adapted for gum massage.

The devices of FIGS. 1-4 can also be adapted for gum massage. Referring to FIG. 5, the bands 120, 122 may have soft liners 124, 126 which contact the gums throughout the mouth, replacing the bristles of the previous embodiments. The liner could be made from various material, including rubber and elastomeric material. The device includes a drive assembly 129, with a motor shown generally at 127, such as that used in FIG. 1 and could include a control 130 to increase or decrease the intensity of movement of the bands and/or the frequency thereof, or to have a selected on/off cycle.

The above-described devices all save considerable time in the teeth cleaning process. Inner and outer surfaces are cleaned, as well as the top surfaces of the molars. With a conventional power toothbrush, two minutes of brushing time is recommended. The self-contained intraoral brush described herein can produce the same cleaning coverage in 4-6 seconds if all the teeth are covered at once. If the device covers only one set (upper or lower jaw) at a time, then the required time could be doubled, i.e. 8-12 seconds.

A further advantage of the device is that the movement of the bands is mechanically limited so as to prevent excessive force/pressure on the teeth or gums of the user.

Hence, several embodiments have been disclosed for a self-contained intraoral dental appliance which comprise two bands with bristles for cleaning. In some of the embodiments, for instance, FIG. 2, the two bands are linked by a swash plate, which enables coverage of the complete surface of the teeth, including the top surface. This arrangement helps to retain the toothpaste in the mouth and helps to maintain the position of the device in the mouth. The bands are driven by a motor(s) which are connected to the bands in such a manner as to produce a generally small circular action of the bands, resulting in a desired cleansing action.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. A self-contained intraoral dental appliance for cleaning teeth, comprising:
   a first substantially rigid band (12) having first and second ends and configured to fit along outer surfaces of at least one entire row of teeth in a user's mouth;
   a second substantially rigid band (14) having first and second ends and configured to fit along inner surfaces of said one row of teeth wherein the first band fits along the outer surfaces of said one entire row of teeth when the second band fits along the inner surfaces of said one row of teeth;
   a motor assembly (20), including a battery (23), for driving the first and second bands;
   an assembly (22, 24, 28, 34, 40, 44) connecting the motor to the first and second bands such that the first end of the first band moves through a displacement path along said one row of teeth while the second end thereof remains substantially stationary, and such that the first end of the second band moves through a displacement path along said row of teeth while the second end thereof remains substantially stationary wherein the first end of the first band and the second end of the second band are located at one side of the user's mouth and wherein the first end of the second band and the second end of the first band are located at the other side of the user's mouth when the appliance is in place in the user's mouth; and
   brush elements (16, 18) attached to the bands, with such a configuration that the teeth are cleaned in operation of the appliance.

2. The dental appliance of claim 1, wherein the brush elements are configured to give substantially complete coverage of the outer and inner surfaces of said one row of teeth during operation of the appliance.

3. The dental appliance of claim 1, wherein the intraoral appliance is configured and arranged to provide cleaning for said one row of teeth, without moving the appliance to successive positions in the mouth.

4. The dental appliance of claim 1, wherein the intraoral appliance is configured and arranged to provide cleaning all the teeth in the mouth.

5. The dental appliance of claim 1, wherein the motor rotates at a speed within the range of 5-150 Hz.

6. The dental appliance of claim 5, wherein the range is 30-100 Hz.

7. The dental appliance of claim 1, wherein the first end (26) of the first band and the first end (38) of the second band are eccentrically mounted on a motor drive shaft (22, 24), and wherein the second end (30) of the first band and the second end (42) of the second band are concentrically mounted on the motor drive shaft.

8. The dental appliance of claim 7, wherein the motor (20) and the motor drive shaft (22, 24) extend substantially in a plane of first end and the second end of each of the first and second bands.

9. The dental appliance of claim 1, wherein the appliance includes an additional first band and an additional second band, to cover all the teeth in the mouth.

* * * * *